United States Patent [19]
Berg

[11] Patent Number: 5,846,229
[45] Date of Patent: *Dec. 8, 1998

[54] CATHETER FOR THE RIGHT CORONARY ARTERY

[75] Inventor: Todd A. Berg, Lino Lakes, Minn.

[73] Assignee: Scimed Life Systems, Inc., Maple Grove, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 656,570

[22] Filed: May 31, 1996

[51] Int. Cl.$^6$ ................................................. A61M 25/00
[52] U.S. Cl. .......................... 604/281; 604/280; 604/264
[58] Field of Search ................................. 604/280–281, 604/264

[56] References Cited

U.S. PATENT DOCUMENTS

| | | |
|---|---|---|
| 4,215,703 | 8/1980 | Willson . |
| 4,838,879 | 6/1989 | Tanabe et al. . |
| 4,883,058 | 11/1989 | Ruiz . |
| 4,935,017 | 6/1990 | Sylvanowicz . |
| 4,973,306 | 11/1990 | Ruiz . |
| 5,016,640 | 5/1991 | Ruiz . |
| 5,195,990 | 3/1993 | Weldon . |
| 5,215,540 | 6/1993 | Anderhub . |
| 5,299,574 | 4/1994 | Bower . |
| 5,306,263 | 4/1994 | Voda . |
| 5,348,545 | 9/1994 | Shani et al. . |
| 5,401,258 | 3/1995 | Voda . |
| 5,476,453 | 12/1995 | Mehta . |

OTHER PUBLICATIONS

Diagnostic Radiology Catheter Shapes, 1994 Cordis Catalog (6 pages).
Manual of Interventional Cardiology, Mark Freed, M.D. and Cindy Grines, M.c. Editors 1992 (3 pages).
Innovations for Safer Angiography and Angioplasty, Shneider Shiley Product Catalog (5 page).
Hospital Price List, USCI Division, C.R. Bard, Inc., Effective Jan. 1, 1986 (20 pages).

*Primary Examiner*—Wynn Wood Coggins
*Assistant Examiner*—Deborah Blyveis
*Attorney, Agent, or Firm*—Robert E. Atkinson

[57] ABSTRACT

A catheter for the right coronary artery where the catheter includes a substantially straight proximal shaft section and a distal shaft section. The distal shaft section includes a support arm which is sized to traverse the aortic root such that the one end of the support arm rests against the aortic wall opposite the right coronary ostium and the other end of the support arm rests in the right coronary ostium. The support arm provides for increased back-up support by utilizing the opposite aortic wall. The distal shaft section further includes a tertiary curve disposed proximal of the support arm. The tertiary curve has an arc angle of less than about 90 degrees such that torque may be readily transmitted from the proximal shaft section to the support arm thereby facilitating controlled tip manipulation. Methods of using such a catheter are also disclosed.

20 Claims, 1 Drawing Sheet

CATHETER FOR THE RIGHT CORONARY ARTERY

FIELD OF THE INVENTION

The present invention generally relates to medical devices. More specifically, the present invention relates to catheters for the right coronary artery. Those skilled in the art will recognize the benefits of applying the present invention to similar fields not discussed herein.

BACKGROUND OF THE INVENTION

Coronary artery disease is commonly treated by relatively non-invasive techniques such as percutaneous translumenal coronary angioplasty (PTCA). Conventional PTCA is well known in the art and typically involves the use of a balloon catheter, possibly in combination with other intravascular devices such as a guide wire and a guide catheter. A typical balloon catheter has an elongate shaft with a balloon attached to its distal end and a manifold attached to its proximal end. In use, the balloon catheter is advanced into a guide catheter and over a guide wire such that the balloon is positioned adjacent a restriction in a diseased coronary artery. The balloon is then inflated and the restriction in the vessel is opened.

Guide catheters typically include an elongate tube with a relatively straight proximal section and a shaped (e.g., curved) distal section. The distal section is shaped to navigate over the aortic arch and seat in the ostium of either the right or left coronary artery. The size and shape of the distal section is dictated in part by the size of the aortic root, the location of the ostium and the take-off angle of the coronary artery. The size and shape of the distal section may affect the ability of the treating physician to access a particular coronary artery, the ease of gaining such access and the back-up support provided to devices passing inside the catheter once access is established.

The right coronary artery is commonly accessed using either a Judkins Right (JR), a Voda Right (VR), an Amplatz Right (AR), a Hockey Stick (HS) or a Multipurpose (MP) catheter, all of which are well known in the art. Although all of these curve styles offer a varying degree of back-up support and catheter tip orientation, no single curve style provides both optimal back-up support and optimal catheter tip orientation combined with controlled tip manipulation.

SUMMARY OF THE INVENTION

The present invention overcomes the disadvantages of the prior art catheter designs by providing a catheter for use in the right coronary artery that provides both optimal back-up support and optimal catheter tip orientation combined with controlled tip manipulation.

The present invention may be described as a catheter for the right coronary artery where the catheter includes a substantially straight proximal shaft section and a distal shaft section. The connection between the proximal shaft section and the distal shaft section may be integral or non-integral. The distal shaft section includes a support arm which is sized to traverse the aortic root such that the one end of the support arm rests against the aortic wall opposite the right coronary ostium and the other end of the support arm rests in the right coronary ostium. The support arm provides for increased back-up support by utilizing the opposite aortic wall. The distal shaft section further includes a tertiary curve disposed proximal of the support arm. The tertiary curve has an arc angle of less than about 90 degrees such that torque may be readily transmitted from the proximal shaft section to the support arm thereby facilitating controlled tip manipulation.

The support arm may include a primary curve located near the distal end of the distal shaft section, a secondary curve located proximal of the primary curve and a substantially straight transition segment disposed between the primary curve and the secondary curve.

The primary curve may have a radius of about 1 to 3 centimeters and an arc angle of about 15 to 90 degrees so as to position the distal end of the distal shaft section in the ostium of the right coronary artery and so as to provide for varying take-off angles of the right coronary artery.

The secondary curve may have a radius of about 1 to 3 centimeters and an arc angle of about 45 to 180 degrees so as to define a gentle curvature for a device passing inside the catheter.

The transition portion may have a length of about 0.5 to 1.6 centimeters such that the length from the distal end of the distal shaft section to the apex of the secondary curve is approximately equal to the distance from the ostium of the right coronary artery to the opposite aortic wall.

The present invention may also be described as a method of using a catheter for the right coronary artery where the method includes the following steps: (a) providing a catheter as described above; (b) advancing the catheter over the aortic arch with the inside curvature of the support arm facing the aortic wall opposite the right coronary artery; and (c) rotating the proximal shaft section until the distal shaft section rotates to seat the tip in the right coronary ostium.

Other aspects and advantages of the present invention can be fully appreciated with a thorough review of the entire specification and drawings. Those skilled in the art will appreciate other advantages not fully described herein. Furthermore, while the disclosure focuses on guide catheters, those skilled in the art will recognize that the invention may be incorporated into other devices and methods of use without departing from the spirit of the invention.

DETAILED DESCRIPTION OF THE INVENTION

The following detailed description should be read with reference to the drawings in which similar parts in different drawings are numbered the same. The drawings, which are not necessarily to scale, depict exemplary embodiments and are not intended to limit the scope of the invention.

Examples of materials, dimensions, assemblies and manufacturing processes are provided for selected parts. All other parts employ that which is known to those skilled in the field of the invention. Those skilled in the art will recognize that many of the examples provided have suitable alternatives which may also be utilized.

Those skilled in the art will also recognize that the present invention may be utilized in the form of a guide catheter, a diagnostic catheter, or any other catheter that employs a shaped distal section designed for a specific anatomical geometry.

Figure 1:
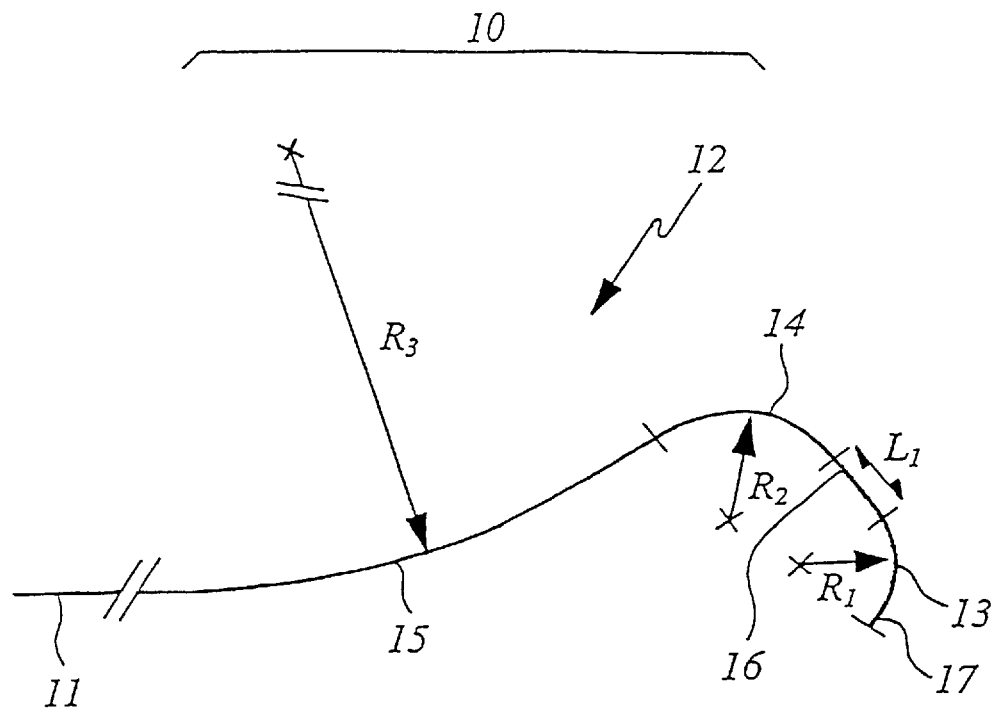
FIG. 1 illustrates a catheter of the present invention in a relaxed state.

With reference to FIG. 1, catheter 10 is shown in a relaxed state. Catheter 10 may be manufactured by several methods known in the art utilizing various materials also known in the art. For example, catheter 10 may be formed of a multilayer extrusion including an inner layer made of a lubricious polymer, a middle layer made of a metal coil or braid for added torque transmission and an outer layer made of a polymer for added stiffness. The catheter of the present invention may also be formed of different materials or constructions along its length to impart varying flexibility and varying radiopacity.

An example of a particularly suitable construction for a guide catheter application is a composite tube. The inner layer may be formed of a lubricious polymer such as PTFE having a wall thickness of about 0.0015 inches. The middle layer may be formed of a stainless steel braid having a fiber diameter of about 0.002 inches and a tensile strength of about 340 kpsi. The middle layer may be braided directly on the inner layer. The outer layer may be formed of a polyether-amide material having a durometer on the order of 63 to 72 Shore D. The outer layer may be extruded directly over the inner and middle layers in order to form a composite tube. In addition, the outer layer may be filled with a radiopaque agent to enhance visualization under x-ray. A soft polyether-amide material having a durometer on the order of 25 to 40 Shore D may be thermally fused to the distal end of the catheter to provide an atraumatic tip. The distal end of the catheter may be thermally formed to virtually any desired shape. Typical dimensions for a guide catheter include an outer diameter ranging from 6 F to 10 F and an inner diameter ranging from 0.060 to 0.110 inches.

A diagnostic catheter may be constructed in a similar manner as a guide catheter except that the inner layer may be formed of a different polymer such as nylon or polyurethane. In addition, the middle layer may be formed of a low tensile strength stainless steel. Typical dimensions for a diagnostic catheter include an outer diameter ranging from 5 F to 7 F and an inner diameter ranging from 0.045 to 0.065 inches.

With continued reference to FIG. 1, catheter 10 includes a proximal shaft section 11 that is substantially straight in a relaxed state. Catheter 10 also includes a distal shaft section 12 connected to the distal end of the proximal shaft section 11. The shape of the distal shaft section 12 may be formed utilizing conventional thermoforming techniques. The connection between the proximal shaft section 11 and the distal shaft section 12 may be integral or non-integral.

Distal shaft section 12 includes a primary curve 13 located proximate the distal end of the distal shaft section 12. An a traumatic tip 17 is disposed at the distal end of the distal shaft section 12. Distal shaft section 12 also includes a secondary curve 14 disposed proximal of the primary curve 13. The secondary curve 14 and the primary curve 13 are separated by a substantially straight transition segment 16. Distal shaft section 12 further includes an oppositely-facing tertiary curve 15 disposed proximal of the secondary curve 14.

The secondary curve 14 has an apex (not labeled) generally disposed in the middle of the curve 14. The portion of the distal shaft section 12 which includes the primary curve 13, the transition segment 16 and the secondary curve 14 up to the apex may be collectively referred to as a support arm.

Each of the primary 13, secondary 14 and tertiary 15 curves has a radius (labeled $R_1$, $R_2$ and $R_3$ respectively) and an arc angle (not labeled). Transition section 16 is substantially linear and has a length (labeled $L_1$). Proximal shaft section 11 is substantially linear and has a length that is conventional in the art. The following table illustrates the range of dimensions and the preferred dimensions for each part of the distal shaft section 12.

TABLE 1

| PART & PARAMETER | RANGE | PREFERRED RANGE | PREFERRED DIMENSION |
| --- | --- | --- | --- |
| Primary Curve Radius | 1.0–3.0 cm | 1.5–2.5 cm | 1.9 cm |
| Primary Curve Arc Length | 15–90 degrees | 60–80 degrees | 63 degrees |
| Secondary Curve Radius | 1.0–3.0 cm | 1.5–2.5 cm | 1.9 cm |
| Secondary Curve Arc Length | 45–180 degrees | 75–180 degrees | 90 degrees |
| Tertiary Curve Radius | 5–25 cm | 10–20 cm | 12 cm |
| Tertiary Curve Arc Length | 15–90 degrees | 30–50 degrees | 37 degrees |
| Transition Segment Length | 0.0–2.0 cm | 0.0–1.6 cm | 0.8 cm |

Figure 2:
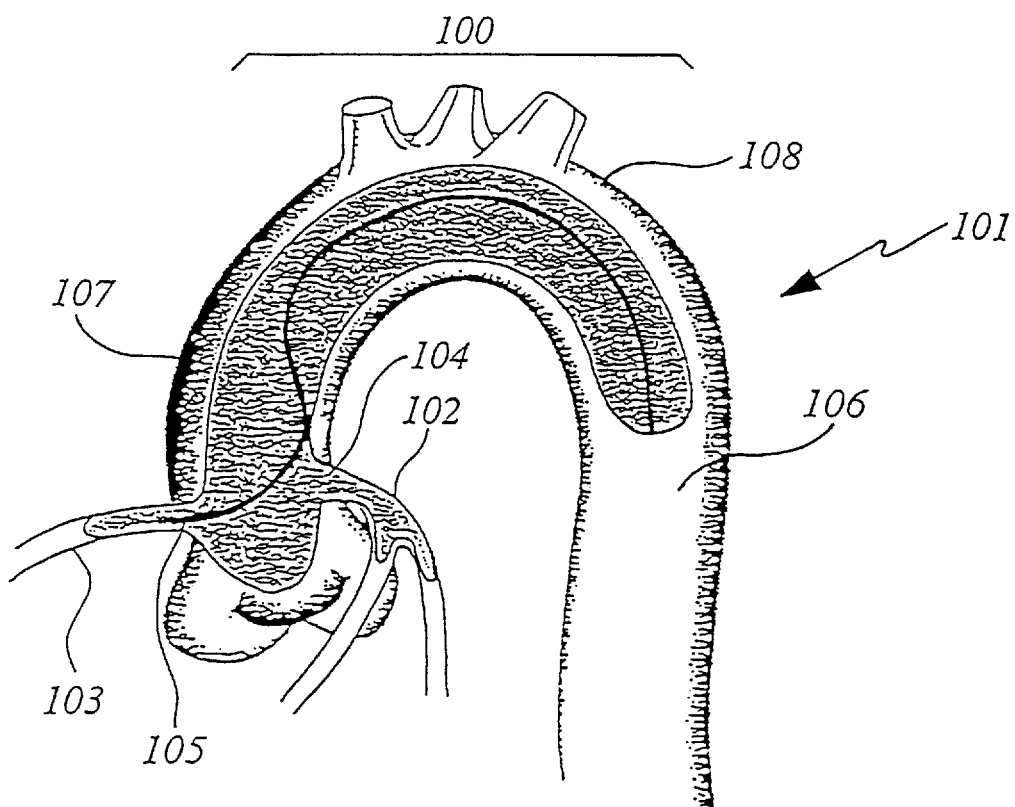
FIG. 2 illustrates a catheter of the present invention as it would appear inside the human body.

Refer now to FIG. 2 which illustrates catheter 10 of the present invention as it would appear inside the human body. In-vivo model 100 shows part of a typical coronary anatomy including the aorta 101 and the coronary arteries 102 and 103. The aorta 101 includes the descending aorta 106 and the ascending aorta 107 separated by the aortic arch 108. The left anterior descending (LAD) artery 102 and the right coronary artery (RCA) 103 are positioned in the root of the ascending aorta 107. Relative to the RCA 103, the LAD 102 is positioned on the opposite wall of the ascending aorta 107. Both the LAD 102 and the RCA 103 include an ostium 104, 105 respectively which define entry ports for blood flow from the ascending aorta 107. Blood flows from the ascending aorta 107 into the left ostium 104 and the right ostium 105 and through the LAD 102 and RCA 103 which provide oxygenated blood to the heart muscle.

As seen in FIG. 2, the distal tip 17 of the distal shaft section 12 is seated in the ostium 105 of the RCA 103. The support arm (i.e, the primary curve 13, the transition section 16 and the secondary curve 14 up to the apex) is sized to traverse the aortic root such that the one end of the support arm rests against the aortic wall opposite the RCA 103 and the other end of the support arm rests in the right coronary ostium 105. The support arm provides excellent back-up support by utilizing the aortic wall opposite the right ostium 105 and opposite the RCA 103.

The primary curve 13 is dimensioned to position the catheter tip 17 inside the right ostium 105. The primary curve is also dimensioned to accommodate a wide range of take-off angles of the RCA 103.

As best illustrated in FIG. 2, the secondary curve 14 gradually transitions the direction of the distal section 12 from a generally vertical orientation to a generally horizontal orientation. The gentle curvature of the secondary curve 14 provides a smooth path for devices passing inside the catheter 10.

Together with the primary curve 13 and the secondary curve 14, the transition segment 16 is dimensioned to bring the primary curve 13 into engagement with the right coronary ostium 105 and the apex of the secondary curve 14 into engagement with the opposite aortic wall just above the left ostium 104.

The tertiary curve 15 is a relatively shallow curve such that torque may be readily transmitted from the proximal shaft section 11 to the support arm thereby facilitating controlled manipulation of the tip 17 into the right coronary ostium 105. The tertiary curve centers the distal shaft section 12 in the ascending aorta 107 and helps navigate the support arm into proper position.

Catheter 10 may be used in the conventional manner except as described hereinafter. The catheter 10 is advanced up and over the aortic arch 108 with the inside curvature of the primary 13 and secondary 14 curves facing the aortic wall opposite the RCA 103. Once the distal shaft section 12 is in the root of the ascending aorta 107, the proximal shaft section 11 is rotated or torqued until the distal shaft section 12 rotates to seat the tip 17 in the right ostium 105. The tip 17 is biased into the right ostium 105 by virtue of the size of the support arm relative to the inside diameter of the aortic root. With the catheter 10 fully engaged, various conventional diagnostic or therapeutic procedures may be performed utilizing catheter 10.

While the specification describes the preferred constructions, materials, dimensions, methods of manufacture and methods of practice, those skilled in the art will appreciate the scope and spirit of the invention with reference to the appended claims.

What is claimed is:

1. A catheter for the right coronary artery, the catheter comprising:
a substantially straight proximal shaft section having a proximal end and a distal end; and a distal shaft section having a proximal end and a distal end, the proximal end of the distal shaft section connected to the distal end of the proximal shaft section, the distal shaft section including a support arm having a proximal portion and a distal portion, the support arm sized to traverse the aortic root such that the proximal portion of the support arm rests against the aortic wall opposite the right coronary ostium and the distal portion of the support arm rests in the right coronary ostium thereby providing increased back-up support utilizing the opposite aortic wall, the distal shaft section further including a tertiary curve having a proximal end and a distal end, the proximal end of the tertiary curve connected to the distal end of the proximal shaft section and the distal end of the tertiary curve connected to the proximal end of the support arm wherein the tertiary curve has a radius of about 10 to 20 centimeters and an arc angle of less than about 90 degrees such that torque may be readily transmitted from the proximal shaft section to the support arm thereby facilitating controlled tip manipulation.

2. A catheter for the right coronary artery as in claim 1, wherein the tertiary curve has a radius of about 10 to 20 centimeters and an arc angle of less than about 45 degrees.

3. A catheter for the right coronary artery as in claim 1, wherein the support arm includes a primary curve proximate the distal end of the distal shaft section, a secondary curve located proximal of the primary curve and a substantially straight transition portion disposed between the primary curve and the secondary curve.

4. A catheter for the right coronary artery as in claim 3, wherein the primary curve has a radius of about 1 to 3 centimeters and an arc angle of about 15 to 90 degrees so as to position the distal end of the distal shaft section in the ostium of the right coronary artery and so as to provide for varying take-off angles of the right coronary artery.

5. A catheter for the right coronary artery as in claim 4, wherein the secondary curve has a radius of about 1 to 3 centimeters and an arc angle of about 45 to 180 degrees so as to define a gentle curvature for a device passing inside the catheter.

6. A catheter for the right coronary artery as in claim 5, wherein the transition portion has a length of about 0.5 to 1.6 centimeters such that the length from the distal end of the distal shaft section to the apex of the secondary curve is approximately equal to the distance from the ostium of the right coronary artery to the opposite aortic wall.

7. A catheter for the right coronary artery as in claim 6, wherein the tertiary curve has a radius of about 10 to 20 centimeters and an arc angle of less than about 45 degrees.

8. A catheter for the right coronary artery as in claim 7, wherein the primary curve has a radius of about 1.9 centimeters and an arc angle of about 63 degrees.

9. A catheter for the right coronary artery as in claim 8, wherein the secondary curve has a radius of about 1.9 centimeters and an arc angle of about 90 degrees.

10. A catheter for the right coronary artery as in claim 9, wherein the transition portion has a length of about 0.8 centimeters.

11. A catheter for the right coronary artery, the catheter comprising:
a substantially straight proximal shaft section having a proximal end and a distal end; and a distal shaft section having a proximal end and a distal end, the proximal end of the distal shaft section connected to the distal end of the proximal shaft section, the distal shaft section including a primary curve proximate the distal end, a secondary curve located proximal of the primary curve, a substantially straight transition portion disposed between the primary curve and the secondary curve, and an oppositely-facing tertiary curve having a proximal end and a distal end, the proximal end of the tertiary curve connected to the distal end of the proximal shaft section and the distal end of the tertiary curve connected to the proximal end of the secondary curve, wherein the length from the distal end of the distal shaft section to the apex of the secondary curve is approximately equal to the distance from the ostium of the right coronary artery to the opposite aortic wall thereby providing increased back-up support utilizing the opposite aortic wall, and further wherein the tertiary curve has an arc angle of less than about 90 degrees such that torque may be readily transmitted from the proximal shaft section to the support arm thereby facilitating controlled tip manipulation.

12. A catheter for the right coronary artery as in claim 11, wherein the connection between the proximal shaft section and the distal shaft section is integral.

13. A catheter for the right coronary artery as in claim 11, wherein the primary curve has a radius of about 1 to 3 centimeters and an arc angle of about 15 to 90 degrees so as to position the distal end of the distal shaft section in the ostium of the right coronary artery and so as to provide for varying take-off angles of the right coronary artery.

14. A catheter for the right coronary artery as in claim 13, wherein the secondary curve has a radius of about 1 to 3 centimeters and an arc angle of about 45 to 180 degrees so as to define a gentle curvature for a device passing inside the catheter.

15. A catheter for the right coronary artery as in claim 14, wherein the transition portion has a length of about 0.5 to 1.6 centimeters such that the length from the distal end of the distal shaft section to the apex of the secondary curve is approximately equal to the distance from the ostium of the right coronary artery to the opposite aortic wall.

16. A catheter for the right coronary artery as in claim 15, wherein the tertiary curve has a radius of about 10 to 20 centimeters and an arc angle of less than about 45 degrees.

17. A catheter for the right coronary artery as in claim 16, wherein the primary curve has a radius of about 1.9 centimeters and an arc angle of about 63 degrees.

18. A catheter for the right coronary artery as in claim 17, wherein the secondary curve has a radius of about 1.9 centimeters and an arc angle of about 90 degrees.

19. A catheter for the right coronary artery as in claim 18, wherein the transition portion has a length of about 0.8 centimeters.

20. A catheter for the right coronary artery as in claim 11, wherein the tertiary curve has a radius of about 10 to 20 centimeters and an arc angle of less than about 45 degrees.

\* \* \* \* \*

UNITED STATES PATENT AND TRADEMARK OFFICE
CERTIFICATE OF CORRECTION

PATENT NO. : 5,846,229  
DATED : December 8, 1998  
INVENTOR(S) : BERG

PAGE 1 of 2

It is certified that error appears in the above-identified patent and that said Letters Patent is hereby corrected as shown below:

Item [56],

On the title page, at References Cited, U.S. PATENT DOCUMENTS, insert the following:

| | | | |
|---|---|---|---|
| --4,784,639 | 11/1988 | Patel | 604/53 |
| 4,790,831 | 12/1988 | Skribiski | 604/282 |
| 4,898,591 | 2/1990 | Jang et al. | 604/282 |
| 5,058,595 | 10/1991 | Kern | 128/662.06 |
| 5,322,509 | 6/1994 | Rickerd | 604/53 |
| 5,445,625 | 8/1995 | Voda | 604/281 |
| 5,569,218 | 10/1996 | Berg | 604/282-- |

On the title page, at References Cited, insert:

--FOREIGN PATENT DOCUMENTS

| | | | |
|---|---|---|---|
| WO 92/15356 | 9/1992 | WIPO | 604/280 |
| WO 93/21983 | 11/1993 | WIPO | 604/280-- |

UNITED STATES PATENT AND TRADEMARK OFFICE
CERTIFICATE OF CORRECTION

PATENT NO. : 5,846,229

DATED : December 8, 1998

INVENTOR(S) : BERG

It is certified that error appears in the above-identified patent and that said Letters Patent is hereby corrected as shown below:

On the title page, at References Cited, OTHER PUBLICATIONS, line 5, "M.c." should be --M.D.--; at line 7, "Shneider" should be --Schneider--.

Signed and Sealed this

Eleventh Day of January, 2000

Attest:

Q. TODD DICKINSON

Attesting Officer

Acting Commissioner of Patents and Trademarks